United States Patent [19]

De Boeck et al.

[11] Patent Number: 5,000,938

[45] Date of Patent: Mar. 19, 1991

[54] PROTECTIVE AERATED FOAM HAND LOTION AND PROCESS FOR PREPARING THE SAME

[75] Inventors: Jean M. De Boeck, Brussels Ohain; Michael Maes, Polleur, both of Belgium

[73] Assignee: Innovatec S.A., Brussels, Belgium

[21] Appl. No.: 376,581

[22] Filed: Jul. 7, 1989

Related U.S. Application Data

[63] Continuation-in-part of Ser. No. 231,344, Aug. 12, 1988, abandoned.

[51] Int. Cl.$^5$ .......................... A61K 7/48; A61K 9/10; A61K 9/12
[52] U.S. Cl. ........................................ 424/47; 514/63; 514/938
[58] Field of Search ..................... 514/63, 938; 424/47

[56] References Cited

PUBLICATIONS

Sagarin, *Cosmetics Science & Technology*, 1957, pp. 99–106 and 137–143.
Chemical Abstracts, 1981, vol. 99:58222j.
Chemical Abstracts, 1982, vol. 96:187110h.
Chemical Abstracts, 1982, vol. 96:91498q.
Chemical Abstracts, 1982, vol. 96:183225b.
Chemical Abstracts, 1982, vol. 96:148993d.

Primary Examiner—Dale R. Ore
Attorney, Agent, or Firm—Harpman & Harpman

[57] ABSTRACT

A compound of small amounts of skin protectants and a relatively large amount of deionized water in a lightweight cellular foam or froth resulting from the introduction of gas bubbles during manufacture enables the small amounts of protectants to penetrate the surface of the skin and form an active protective film in the upper layers of the epidermis so as to provide a barrier between the skin surface and the sensitive lower layers of the epidermis. An optimum degree of protection of the skin results from the penetration of the small amounts of the ingredients of the compound which includes propylene glycol, glycerine, sorbitol, stearin, mineral oil, polydimethylsiloxane, sorbitan monostearate, POE sorbitan monostearate, triethanlomaine, and a perfume oil in a combined total of 20% or less of the compound and 80% or more deionized water. Processing the lotion-like compound with a desirable gas liquid forms a cellular foam in which bubbles of gas are contained spacing and diluting the very small amount of ingredients in the foamed lotion-like liquid which results in a quantity controlled application of the ingredients to the skin and greatly expedites the ability of the ingredients to penetrate the skin and form a barrier beneath the skin surface.

7 Claims, No Drawings

PROTECTIVE AERATED FOAM HAND LOTION AND PROCESS FOR PREPARING THE SAME

This is a continuation-in-part of application Ser. No. 07/231,344, filed Aug. 12, 1988, now abandoned.

BACKGROUND OF THE INVENTION

1. Technical Field

This invention relates to penetrating skin protectants for application to human skin for protecting the same against aggressive, irritating and soiling agents.

2. Description of the Prior Art

Skin protectants heretofore known have generally comprised emollients, ointments and creams such as used in the long term care of incontinent geriatric and para/quadraplegic skin. Such emollients, ointments and creams have also been applied to folds of skin subject to perspiration irritation, to dry or cracked skin and to pressure sensitive areas and for ostomy care. A typical emollient ointment or cream contains water and a hydrophobic lanolin, paraffin oil, beeswax and white petrolatum as they form an oily film on the skin that aids in rehydration of the epidermis by partial retention of water.

Many of the emollients include wax esters, such as lanolin spermaceti and beeswax. Others include steroid alcohols, such as cholesterol and other lanolin alcohols. Fatty alcohols are often used and include lauryl, cetyl oleyl and steryl alcohols along with triglyceride esters including animal and vegetable fats and oils. Silicone oils are generally used to modify petrolatum and mineral oil and provide a desirable emollient behavior and these materials, with the exception of water, are the major vehicles used in cosmetic emulsions and serve primarily to carry other emollients. They usually remain on the surface of the skin and cause the corneum to hydrate since water is supplied from the underlying tissues of the skin but is prevented from evaporating to the environment by the hydrocarbon barrier. The normally used quantities of hydrocarbon oils and waxes form barriers to penetration of more effective ingredients.

In all of these prior art compounds, the several ingredients treated the surface of the skin with little or no penetration and were generally capable of being removed by simple washing procedures. None of the prior art compounds known to us are capable of penetrating into the skin and forming an active protective film in the upper layers of the epidermis (corneum stratum).

The compound of the present invention provides a barrier between the skin surface and the very sensitive lower layers of the epidermis which protects the skin from most of the acid and alkaline products, alcohols and detergents in common use. The compound of the present invention enables dirt and other soil to be washed off of the skin much easier and the same is true of the removal of coloring dyes, glues, greases, oils and the like.

The compound of the present invention is completed as a gas liquid lotion foam in aerosol in which bubbles of gas are contained in a very small volume of liquid carrying the ingredients and is easily and quickly applied to the skin where it is absorbed and does not affect sense of touch and due to the small quantity of the compound applied, allows the skin to breath and perspire. The foamed gas liquid lotion of the present invention when applied to the skin is water and soap resistant during about three to four hours after application and in addition to protecting the skin against retention of dirt and soil, coloring dyes, glues, greases, oils, and the like, it additionally protects the skin against chapping, contact allergies, and mild chemical induced irritation.

The present invention may be summarized as a novel, aerated foamed lotion incorporating small amounts of ingredients including stearin, propylene glycol, glycerine and sorbitol combined in a desirable ratio with very small quantities of mineral oil, polydimethylsiloxane, sorbitan monostearate, POE sorbiton monostearate, triethanolamine, and a perfume oil that improve penetration of the active ingredients into the skin, insure emulsification and function as a ph regulator together with a very large amount of deionized water. The resulting lotion compound after mixing is then subjected to a dispersion medium such as a gas, for example 75% N-butane and 25% propane at a suitable gas pressure so as to create a lightweight cellular foam or froth which results from the introduction of gas bubbles into the largely aqueous lotion.

DESCRIPTION OF THE PREFERRED EMBODIMENT

A desirable form of the invention comprises a blend of the several ingredients in a substantially aqueous composition for protective treatment of the skin and comprises the active ingredients stearin, a glycerol ester of stearic acid and palmitic acid, propylene glycol, glycerine and sorbitol, a hexahydric alcohol, isomeric with manitol. Such ingredients together comprise 16½% by weight of the total formula and an additional 3½% by weight of the total formula comprise mineral oil, polydimethylsiloxane, sorbitan monostearate. POE sorbitan monostearate, triethanolamine, and perfume oil such as Sacha A 236,286 (trademark) for a musky, floral green fresh perfume.

The above two groups of ingredients total 20% by weight of the complete formula, the balance of 80% comprising deionzed water.

A specific formula of the foregoing ingredients comprising about 7.50% by weight stearin, about 4% by weight propylene glycol, about 3.50% by weight glycerine, about 1.50% by weight sorbitol, about 1% by weight mineral oil, about 1% by weight polydimethylsiloxane, about 0.65% by weight sorbitan monostearate, about 0.35% by weight POE sorbitan monostearate, about 0.30% by weight triethanolamine, about 0.20% by weight perfume oil, such as Sacha A 236,286 (trademark) for a musky, floral green fresh perfume, and deionzed water about 80% by weight.

The above ingredients are suitably mixed as hereinafter set forth and subjected to a dispersion medium such as a gas, for example 75% N-butane and 25% propane with a gas pressure of about 58 PSI (4 bars) which results in a lightweight cellular foam or froth as occurs from the introduction of gas bubbles during pressurization. The processed lotion-like compound with its desirable gas liquid cellular foam in which the bubbles of gas are contained in a small volume of liquid advantageously spaces and dilutes the small amount of lotion enabling the processed foamed lotion to be applied to the skin in controlled amounts contributing to the successful penetration of the several ingredients into the skin to form a barrier between the skin surface and the sensitive lower layers of the epidermis.

The foamed lotion is inoffensive, colorless, non-greasy, inperceptible shortly after its application due to its dilution in the foam and its rapid absorption by the skin. The product enables the skin to retain a full sense of touch and it allows the skin to breath and perspire, all of which are desirable attributes.

It is believed that a specific process for preparing the foregoing formula is essential and such process comprises; placing the propylene glycol, the glycerine, the sorbitol and the triethanolamine in about one-third of the deionized water in a first receptacle, heating the same to 65° Celsius while slowly stirring the mixture for about 35 minutes, placing the stearin, mineral oil, polydimethylsiloxane, sorbitan monostearate, and POE sorbitan monostearate in a second vessel and heating the same to 65° Celsius and slowly stirring the mixture for about 20 minutes; adding the heated stearin, mineral oil, polydimethylsiloxane, sorbitan monostearate and POE sorbitan monostearate to the heated propylene glycol, glycerine, sorbitol and triethanolamine, and deionized water in the first vessel and mixing thoroughly for about 10 minutes; adding the remaining substantially two-thirds of the deionized water to the first vessel so as to dilute the mixture, cooling the mixture to about 42° Celsius and adding the perfume (fragrance) Sacha A 236,286 (trademark) and mixing thoroughly and continue mixing and cool the formula to 35° Celsius while slowing stirring the mixture for about 20 minutes. The resulting formula is then packaged in a pressurized container in which a dispersion medium, such as the aforementioned gas which may comprise butane and propane, is present and either initiates or continues the foamed form of the formula and insures its delivery in an extremely fine bubble foam form from the pressurized container. The foamed lotion thus formed and dispensed has an unusually dry characteristic feeling upon application to the skin.

It will be understood that a novel foamed and highly effective protective hand lotion and a process for preparing the same has been disclosed which when applied to the human skin, as for example the hands of a person, quickly penetrates into the skin and forms an active protecting film forming a barrier between the skin surface and the sensitive lower layers of the epidermis which is capable of protecting the skin from most acid and alkaline products, alcohol and detergents in common use and which makes washing off dirt, soil, coloring dyes, glues, greases, oils, and the like much easier than heretofore possible.

Additionally, it will be understood that the foamed protective hand lotion ingredients protect the skin against chapping, contact allergies, and minor irritations and shortly after application the product becomes non-visible as it is colorless due to the small quantity of the ingredients of the lotion in the cellular foam and its rapid absorption into the skin where it remains in effective protective position in the skin for at least four hours after application and is not removed during this time by repeated washing.

It has been determined that the hereinbefore stated quantities of the several ingredients may be changed within certain limits without altering the effectiveness of the formula. For example, the formula may comprise from about 7% to about 8% by weight stearin, from about 3.50% to about 4.50% by weight propylene glycol, from about 3.10% to about 3.90% by weight glycerine, from about 1.30% to about 1.70% by weight sorbitol, from about 0.80% to about 1.20% by weight mineral oil, from about 0.80% to about 1.20% by weight polydimethylsiloxane, from about 0.60% to about 0.70% by weight sorbitan monostearate, from about 0.30% to about 0.40% by weight POE sorbitan monostearate, from about 0.25% to about 0.35% by weight triethanolamine, from about 0.15% to about 0.30% by weight perfume oil such as Sacha A 236,286 (trademark), and from about 77.75% to about 82.20% by weight deionized water.

It will be understood that the foregoing ingredients in the ranges specified are mixed and processed in the same manner as hereinbefore described in connection with the specific amounts of the same ingredients and the resulting product processed through the pressurization and packaging whereby the compound of the ingredients in a lightweight cellular form or froth resulting from the introduction of gas bubbles during the manufacture enables small amounts of the compound to penetrate the surface of the skin and form an active protective film in the upper layers of the epidermis so as to provide a barrier between the skin surface and the sensitive lower layers of the epidermis.

Although but one embodiment of the protective gas pressurized foamed substantial aqueous compound for protective treatment of the skin and one process for preparing the same has been described, it will be apparent to those skilled in the art that various changes and modifications may be made in the formula and the process without departing from the spirit of the invention and having thus described our invention what we claim is:

We claim:

1. A gas pressurized foamed substantially aqueous compound for protective treatment of the skin comprising about 4% by weight propylene glycol, about 3.50% by weight glycerin, about 1.50% by weight sorbitol, about 7.50% by weight stearin, about 1% by weight mineral oil, about 1% by weight polydimethylsiloxane, about 0.65% by weight sorbitan monostearate, about 0.35% by weight POE sorbitan monostearate, about 0.30% by weight triethanolamine, about 0.20% by weight musk floral green fresh perfume and about 80% by weight deionized water packaged in a pressurized canister with a gas at about 58 PSI.

2. A foamed substantially aqueous compound for protective treatment of the skin comprising from about 3.50% to about 4.50% by weight propylene glycol, from about 3.10% to about 3.90% by weight glycerine, from about 1.30% to about 1.70% by weight sorbitol, from about 7% to 8% by weight stearin, from about 0.80% to about 1.20% by weight mineral oil, from about 0.80% to about 1.20% by weight polydimethylsiloxane, from about 0.60% to about 0.70% sorbitan monostearate, from about 0.30% to about 0.40% by weight POE sorbitan monostearate, from about 0.25% to about 0.35% by weight triethanolamine, from about 0.15% to about 0.30% by weight of a perfume oil and from about 77.75% by weight to about 82.20% by weight deionized water, said compound being packaged in a pressurized canister with a propellant gas about 58 PSI in the form of a lightweight cellular froth.

3. A process of making a foamed skin protectant which is at least 77.75% deionized water comprising:
(1) mixing propylene glycol, glycerine, sorbitol, triethanolamine and about one-third of said deionized water in a first vessel to form a first mixture;

(2) raising the temperature of said first mixture to about 65° Celsius, while slowing stirring said mixture for about 35 minutes;

(3) mixing stearin, mineral oil, polydimethylsiloxane, sorbitan monostearate and POE sorbitan monostearate in a second vessel to form a second mixture;

(4) raising the temperature of said second mixture to about 65° Celsius while slowly stirring said second mixture for about 20 minutes;

(5) combining said first and second mixture;

(6) adding deionized water to said combined first and second mixtures to bring the deionized water content to at least said 77.75% of said skin protectant and mixing the same thoroughly for about 10 minutes;

(7) cooling the combined mixtures to about 42° Celsius;

(8) adding perfume to the cooled combined mixtures;

(9) mixing and cooling the combined mixtures to about 35° Celsius;

(10) packaging said combined mixtures in a pressurized canister with a gas at a pressure of about 58 PSI to form a lightweight cellular foam.

4. The method of controlling penetration of dirt, oil and grease into the skin comprising applying to the area where control is desired a protective effective amount of a lightweight cellular froth of a lotion having the formula; about 4% by weight propylene glycol, about 3.50% by weight glycerin, about 1.50% by weight sorbitol, about 7.50% by weight stearin, about 1% by weight mineral oil, about 1% by weight polydimethylsiloxane, about 0.65% by weight sorbitan monostearate, about 0.35% by weight POE sorbitan monostearate, about 0.30% by weight triethanolamine, about 0.20% by weight musk floral green fresh perfume and about 80% by weight deionized water packaged in a pressurized canister with a gas at about 58 PSI.

5. The compound of claim 1 wherein the gas is about 75% N-butane and about 25% propane.

6. The compound of claim 2 wherein the gas is about 75% N-butane and about 25% propane.

7. The process of claim 3 wherein the gas is about 75% N-butane and about 25% propane.

* * * * *